(12) United States Patent
Zou et al.

(10) Patent No.: US 8,410,212 B2
(45) Date of Patent: Apr. 2, 2013

(54) ALCOHOL-SOLUBLE RESIN AND A METHOD FOR PREPARING THE SAME

(75) Inventors: Wenjun Zou, Chengdu (CN); Wenjun Zhong, Chengdu (CN); Mingguo Zou, Chengdu (CN); Guangming Li, Chengdu (CN)

(73) Assignees: Wenjun Zou, Chengdu, Sichuan Province (CN); Wenjun Zhong, Chengdu, Sichuan Province (CN)

( * ) Notice: Subject to any disclaimer, the term of this patent is extended or adjusted under 35 U.S.C. 154(b) by 700 days.

(21) Appl. No.: 11/995,667

(22) PCT Filed: Jan. 9, 2006

(86) PCT No.: PCT/CN2006/000025
§ 371 (c)(1),
(2), (4) Date: Sep. 5, 2008

(87) PCT Pub. No.: WO2007/009325
PCT Pub. Date: Jan. 25, 2007

(65) Prior Publication Data
US 2009/0149615 A1    Jun. 11, 2009

(30) Foreign Application Priority Data
Jul. 15, 2005    (CN) .......................... 2005 1 0021271

(51) Int. Cl.
*C08L 31/02*    (2006.01)
(52) U.S. Cl. ........ 524/564; 523/160; 523/161; 524/548; 524/555; 524/556; 524/558; 524/560; 524/561; 524/563

(58) Field of Classification Search ................. 524/548, 524/555, 556, 558, 563, 564, 560, 561; 526/79, 526/86, 210, 219.6, 232.1, 311; 523/160, 523/161
See application file for complete search history.

(56) References Cited

U.S. PATENT DOCUMENTS

| | | | | |
|---|---|---|---|---|
| 3,092,600 | A | * | 6/1963 | Ozawa et al. ................. 524/432 |
| 3,208,963 | A | * | 9/1965 | Jasinski ........................ 524/558 |
| 3,634,329 | A | * | 1/1972 | Chujo et al. .................. 502/167 |
| 4,937,303 | A | * | 6/1990 | Wolf et al. .................... 526/212 |

FOREIGN PATENT DOCUMENTS

| | | |
|---|---|---|
| CN | 85100687 | 4/1985 |
| CN | 1084867 | 9/1992 |
| CN | 1096312 A | 6/1993 |
| CN | 1632028 A | 11/2004 |

* cited by examiner

*Primary Examiner* — David W Wu
*Assistant Examiner* — Marie Reddick
(74) *Attorney, Agent, or Firm* — Greer, Burns & Crain, Ltd.

(57) ABSTRACT

An alcohol-soluble resin and a method for preparing the same, in which the content of vinyl acetate monomer in polymeric raw material is 50% to 90%. In addition, acrylic ester monomer and other reactive functional group-containing compounds have been mixed in the raw material to ensure the performance of resin for special requirements in application. Also provided are products produced by using the resin, such as alcohol-soluble ink, composite adhesive, lustering oil for printing, glazing lacquer for woodware, superficial decorating coatings for plastic materials, safeguard coatings of metal surface and hair colorant, as well as preparation methods.

3 Claims, No Drawings

ALCOHOL-SOLUBLE RESIN AND A METHOD FOR PREPARING THE SAME

FIELD OF THE INVENTION

The present invention relates to an alcohol-soluble copolymeric resin, particularly an alcohol-soluble resin used as a major raw material for preparing alcohol-soluble fine chemical products such as alcohol-soluble ink and alcohol-soluble plastic composite adhesive, and a method for preparing the same.

BACKGROUND OF THE INVENTION

Resin is a kind of main raw material in producing fine chemical products such as ink, adhesive, paint, etc., and the resin is decisive to the performance and cost of these fine chemical products as well as to the kind of solvent to be used for dilution during application. At present, most of the resins for producing the above products are dissolved and diluted with benzenes and ketones. These solvents not only pollute the environment severely, but as they are extracted from petroleum, their costs are also continuously increasing with the rise of the petroleum price. Due to the pressure of both the cost and the environmental protection, there is an increasing demand for resins that are soluble in alcohols. So far, there are several mature alcohol-soluble resins that can be used to produce the above fine chemical products, including alcohol-soluble polyamide resin, alcohol-soluble polyurethane resin, and polyvinyl acetal resin. However, as a result of the high cost of raw materials, the process of production, and other factors, these kinds of resins are rather expensive, which greatly increases the cost of producing the above products. Therefore, there is an urgent demand in the market to reduce the cost of the alcohol-soluble resin.

As vinyl acetate is one of the cheapest and nontoxic monomer materials in the market, and its polymer is soluble in alcohol, the cost of the alcohol-soluble resin that is produced with vinyl acetate as a main raw material can be reduced greatly. But as the glass transition temperature of vinyl acetate homopolymer is 28° C. and the softening point is low, it will be softened and transfigured when heated. In addition, it is easy to absorb moisture, after which the performance of the resin will be greatly affected. Therefore, there is no existing report at home and abroad of using vinyl acetate as a main raw material in the synthesis of alcohol-soluble resins that are up to the requirements of the above products.

SUMMARY OF THE INVENTION

The first object of the present invention is to prepare an alcohol-soluble resin for producing fine chemical products such as ink and the like. Another object of the present invention is to provide a method for producing the said resin and use of the same.

The alcohol-soluble resin provided in the present invention is polymerized by using a raw material containing 50% to 90% w/w of vinyl acetate and azodiisobutyronitrile and/or benzoyl peroxide as initiator.

Particularly, the alcohol-soluble resin of the present invention is prepared by a raw material of the following weight ratio:

| | |
|---|---|
| vinyl acetate | 50% to 90% |
| acrylic ester and/or methacrylic ester | 4% to 35% |
| reactive functional group-containing compound | 6% to 15% |

A final product will be obtained by adding an initiator of 0.1-1.1% of the total weight of the raw material and polymerizing in ester and/or alcohol solvent(s). After screening and comparing, the preferred weight ratio of the raw material is as follows:

| | |
|---|---|
| vinyl acetate | 80% to 90% |
| acrylic ester and/or methacrylic ester | 4% to 10% |
| reactive functional group-containing compound | 6% to 10% |

During preparation, the alcohol-soluble resin of the present invention is obtained by adding azodiisobutyronitrile and/or benzoyl peroxide of 0.2%-0.9% of the total weight of the above raw material as initiator and polymerizing in ester and/or alcohol solvent(s).

The said reactive functional group-containing compound includes one or more selected from the group consisting of acrylic acid, methacrylic acid, butene dioic acid, hydroxyethyl acrylate, hydroxypropyl acrylate, hydroxyethyl methacrylate, hydroxypropyl methacrylate, glycidyl acrylate, glycidyl methacrylate, reaction product of unsaturated acid and diepoxide, acrylamide, methacrylamide, and hydroxymethyl acrylamide.

The method for preparing the alcohol-soluble resin provided in the present invention comprises the following steps:

a) weighing the raw material according to the following content ratio:

Constituent A:

| | |
|---|---|
| vinyl acetate | 25% to 45% |
| acrylic ester and/or methacrylic ester | 1% to 10%, |

Then add alcohol or ester solvent, its amount being 10% to 35% of the total weight of the above vinyl acetate and the acrylic ester and/or methacrylic ester;

Constituent B:

| | |
|---|---|
| vinyl acetate | 25% to 45% |
| acrylic ester and/or methacrylic ester | 3% to 25% |
| reactive functional group-containing compound | 6% to 15% |

An initiator of 0.1%-0.7% of the total weight of the raw material;

Constituent C:

Initiator of 0.1%-0.4% of the total weight of the raw material, dissolved in ester and/or alcohol solvent(s) for use;

The total weight of the above initiators is 0.1%-1.1% of the total weight of the raw material;

b) adding constituent A into a reactor tank, stirring and heating the material up to the reflux temperature;

c) adding constituent B dropwise into the reactor tank in 1.5 to 4 hours, and leave it for further reaction of 1 hour;

d) adding constituent C dropwise into the reactor tank in 0.5 hour after step c, and leave it for further reaction of 2 hours while keeping the material temperature between 70 to 85° C.

e) adding alcohol and/or ester solvent(s) into the reactor tank for dilution according to the concentration requirement of the product, and stirring while cooling it down, and discharging when the temperature of the material in the tank is below 50° C. so that the alcohol-soluble resin of desired concentration is obtained A preferable embodiment of the content ratio of the raw material in step a) is as follows:

Constituent A:

| | |
|---|---|
| vinyl acetate | 40% to 45% |
| acrylic ester and/or methacrylic ester | 2% to 4%, |

Then add alcohol or ester solvent, its amount being 10% to 35% of the total weight of the above vinyl acetate and acrylic ester and/or methacrylic ester;

Constituent B:

| | |
|---|---|
| vinyl acetate | 40% to 45% |
| acrylic ester and/or methacrylic ester | 2% to 6% |
| reactive functional group-containing compound | 6% to 10% | an initiator of 0.1-0.7% of the total weight of the raw material;

Constituent C:

initiator of 0.1%-0.4% of the total weight of the raw material, dissolved in the ester and/or alcohol solvent(s) for use.

The present invention also provides the use of the alcohol-soluble resin in preparing ink, plastic composite adhesive, glazing lacquer for woodware, lustering oil for printing paper and superficial decorating coatings for plastic material, safeguard coatings for metal surface, and hair colorant.

The present invention further provides the ink and plastic composite adhesive prepared with the above alcohol-soluble resin.

Further details of the present invention will be set forth through embodiments as follows. However, the description of those embodiments should not be understood as the limitation to the scope of the present invention. All of the modifications, variations or adaptations of the invention, made within the principles of the invention and based on known or customary practice in the art, shall fall within the limits of the invention.

DETAILED DESCRIPTION OF PREFERRED EMBODIMENTS

Example 1

Preparation of the Alcohol-Soluble Resin of the Present Invention

Equipments: a reactor tank equipped with a stirrer, a reflux condenser, a stainless steel dropper, and a device for heating and temperature controlling are required in accordance with the present invention.

The process of example 1 comprises:

Step 1: Add into the reactor tank constituent A comprising 40 kg of vinyl acetate, 2 kg of ethyl acrylate, 1 kg of methyl acrylate and 3 kg of methyl methacrylate, in addition with solvent of 10 kg of isopropyl alcohol and 5 kg of ethyl acetate for dilution, and heat up the material while stirring;

Step 2: Prepare in the dropper constituent B comprising 40 kg of vinyl acetate, 3 kg of ethyl acrylate, 1 kg of methyl acrylate, 3 kg of methyl methacrylate, 4 kg of acrylic acid, 3 kg of hydroxypropyl acrylate and 0.5 kg of azodiisobutyronitrile, add the same dropwise into the reactor tank in 2 hours after the material in the tank is heated up to the reflux temperature, and then leave it reacting for 1 hour;

Step 3: Dissolve 0.2 kg of azodiisobutyronitrile in 2.5 kg of isopropyl alcohol and 2.5 kg of ethyl acetate, and add dropwise into the reactor tank in 0.5 hour;

Step 4: Add 20 kg of ethyl acetate and 60 kg of industrial alcohol into the reactor tank after a continuously reaction for 2 hours under a constant temperature in the tank, and then cool down and discharge to obtain 200.7 kg of resin with 50% of solid content.

The resin prepared according to the formula of example 1 is most suitable for producing plastic gravure surface printing ink.

Example 2

Preparation of the Alcohol-Soluble Resin of the Present Invention

Weigh the raw materials according to the following content ratio:

Constituent A:

| | |
|---|---|
| vinyl acetate | 40 kg |
| methyl acrylate | 1 kg |
| methyl methacrylate | 7 kg |

With another 15 kg of isopropyl alcohol as diluent;

Constituent B:

| | |
|---|---|
| vinyl acetate | 33 kg |
| methyl acrylate | 2 kg |
| methyl methacrylate | 8 kg |
| methacrylic acid | 3 kg |
| hydroxypropyl acrylate | 3 kg |
| glycidyl acrylate | 3 kg |
| benzoyl peroxide | 0.5 kg |

Constituent C:

0.2 kg of azodiisobutyronitrile dissolved in 2.5 kg of isopropyl alcohol and 2.5 kg of ethyl acetate.

With 20 kg of ethyl acetate and 60 kg of industrial alcohol as diluent and prepared according to the same method as that of Example 1, 200.7 kg of resin with 50% of solid content will be obtained.

The resin prepared according to the formula of example 2 is most suitable for producing heat and steam endurance plastic gravure composite ink.

Example 3

Preparation of the Alcohol-Soluble Resin of the Present Invention

Weigh the raw materials according to the following content ratio:

Constituent A:

| | |
|---|---|
| vinyl acetate | 45 kg |
| methyl acrylate | 1 kg, |

With another 15 kg of absolute alcohol as diluent;

Constituent B:

| | |
|---|---|
| vinyl acetate | 45 kg |
| methyl acrylate | 3 kg |
| methacrylic acid | 6 kg |
| azodiisobutyronitrile | 0.5 kg |

Constituent C:

0.2 kg of azodiisobutyronitrile dissolved in 5 kg of solvent of ethyl acetate.

With 20 kg of ethyl acetate and 60 kg of industrial alcohol as diluent, and prepared according to the same method as that of Example 1, 200.7 kg of resin with 50% of solid content will be obtained.

The resin prepared according to the formula of example 3 is most suitable for producing ordinary plastic gravure composite ink.

Example 4

Preparation of the Alcohol-Soluble Resin of the Present Invention

Weigh the raw materials according to the following content ratio:

Constituent A:

| | |
|---|---|
| vinyl acetate | 25 kg |
| butyl acrylate | 20 kg, |

With another 15 kg of isopropyl alcohol as diluent;

Constituent B:

| | |
|---|---|
| vinyl acetate | 25 kg |
| acrylic acid | 5 kg |
| butyl acrylate | 15 kg |
| hydroxypropyl acrylate | 10 kg |
| azodiisobutyronitrile | 0.7 kg |

Constituent C:

0.2 kg of azodiisobutyronitrile dissolved in 2.5 kg of isopropyl alcohol and 2.5 kg of ethyl acetate.

With 40 kg of ethyl acetate and 40 kg of industrial alcohol as diluent, and prepared according to the same method as that of Example 1, 200.9 kg of resin with 50% of solid content will be obtained.

The resin prepared according to the formula of example 4 is a plastic composite adhesive with 50% of solid content.

Example 5

Preparation of the Alcohol-Soluble Ink of the Present Invention

Formula for producing the alcohol-soluble ink by use of the resin of the present invention is as follows (weight ratio):

| | |
|---|---|
| resin solution prepared in Example 1, 2 or 3 (50% of solid content) | 35 kg |
| titanium white | 35 kg |
| terpene phenolic resin | 1 kg |
| ethyl acetate | 6-9 kg |
| industrial alcohol | 21-24 kg |

Process for producing the alcohol-soluble ink by use of the resin of the present invention is as follows:

Add the above raw materials into a vessel, stir at high speed for 20 minutes for the materials to blend fully and disperse uniformly, and mill in a sand mill with the material's temperature not higher than 40° C. When the fineness is less than 15 micron, the final product is finished.

Example 6

Preparation of the Alcohol-Soluble Resin of the Present Invention

Weigh the raw materials according to the following content ratio:

Constituent A:

| | |
|---|---|
| vinyl acetate | 30 kg |
| methyl acrylate | 2 kg, |

With another 10 kg of isopropyl alcohol as diluent;

Constituent B:

| | |
|---|---|
| vinyl acetate | 30 kg |
| methyl methacrylate | 25 kg |
| methacrylic acid | 3 kg |
| methyl acrylate | 5 kg |
| glycidyl methacrylate | 3 kg |
| cis-butenedioic acid | 2 kg (dissolved in 5 kg of ethanol) |
| benzoyl peroxide | 0.5 kg |

Constituent C:

0.3 kg of benzoyl peroxide dissolved in 5 kg of ethyl acetate;

With 20 kg of ethyl acetate and 60 kg of industrial alcohol as diluent, and prepared according to the same method as that of Example 1, 200.8 kg of resin with 50% of solid content will be obtained.

The resin prepared according to the formula of example 6 is suitable for producing glazing lacquer for woodware, lustering oil for printing paper, and superficial decorating coatings for plastic materials.

Example 7

Preparation of the Glazing Lacquer for Woodware of the Present Invention

Formula for producing the glazing lacquer for woodware by use of the resin of the present invention is as follows (weight ratio):

| | |
|---|---|
| resin solution prepared in Example 6 (50% of solid content) | 45 kg |
| nitrocellulose alcohol solution (70%) | 20 kg |
| dibutyl ester | 3 kg |
| ethyl acetate | 12 kg |
| butanol | 8 kg |
| absolute alcohol | 12 kg |

Process for producing the glazing lacquer for woodware of the present invention is as follows:
Put the above raw materials into a vessel, stir for 10 minutes for them to blend fully and disperse uniformly, and the final product will be obtained after filtering.

Example 8

Preparation of the Lustering Oil for Printing Paper of the Present Invention Formula for producing the lustering oil for printing paper of this example is as follows (weight ratio):

| | |
|---|---|
| resin solution prepared in Example 6 (50% of solid content) | 40 kg |
| alcohol-soluble rosin solution (20% of solid content) | 35 kg |
| gas phased silicon dioxide | 3 kg |
| ethyl acetate | 7 kg |
| butanol | 2 kg |
| absolute alcohol | 13 kg |

The process of this example is as follows:
Put the above raw materials into a vessel, stir at high speed for 30 minutes for them to blend fully and disperse uniformly, and the final product will be obtained after filtering.

Example 9

Preparation of the Alcohol-Soluble Superficial Decorating Coatings for Plastic Materials of the Present Invention Formula for producing the superficial decorating coatings for plastic materials by use of resin of the present invention is as follows (weight ratio):

| | |
|---|---|
| resin solution prepared in Example 6 (50% of solid content) | 45 kg |
| pigment | 20 kg |
| leveling agent | 0.3 kg |
| antisettle agent | 1 kg |
| ethyl acetate | 10 kg |
| butanol | 2 kg |
| absolute alcohol | 21 kg |

The process for producing the superficial decorating coatings for plastic materials by use of resin of the present invention is as follows:
Put the above raw materials into a vessel, stir at high speed for 10 minutes for them to blend fully and disperse uniformly, and the final product will be obtained after milling in a sand mill to make the fineness less than 15 micron.

Example 10

Preparation of the Alcohol-Soluble Resin of the Present Invention

Weigh the raw materials according to the following content ratio:
Constituent A:

| | |
|---|---|
| vinyl acetate | 30 kg |
| methyl acrylate | 4 kg | addition with 10 kg of isopropyl alcohol as diluent;
Constituent B:

| | |
|---|---|
| vinyl acetate | 30 kg |
| methyl methacrylate | 20 kg |
| hydroxypropyl acrylate | 2 kg |
| methyl acrylate | 4 kg |
| methacrylic acid | 5 kg |
| glycidyl methacrylate | 5 kg |
| azodiisobutyronitrile | 0.6 kg |

Constituent C:
0.2 kg of azodiisobutyronitrile dissolved in solvent of 5 kg of ethyl acetate;
With 20 kg of ethyl acetate and 65 kg of industrial alcohol as diluent, and prepared according to the same method as that of Example 1, 200.8 kg of resin with 50% of solid content will be obtained.
The resin prepared according to the formula of example 10 is suitable for producing safeguard coatings of metal surface.

Example 11

Preparation of the Alcohol-Soluble Rotproof Coatings for Metal of the Present Invention Formula for producing the rotproof coatings for metal by use of the resin of the present invention is as follows (weight ratio):

| | |
|---|---|
| resin solution prepared in Example 10 (50% of solid content) | 50 kg |
| titanium white or other material | 15 kg |
| defoaming agent | 0.8 kg |
| leveling agent | 0.2 kg |
| antisettle agent | 1 kg |
| ethyl acetate | 10 kg |
| butanol | 2 kg |
| absolute alcohol | 21 kg |

Process for producing rotproof coatings for metal by use of resin of the present invention is as follows:
Put the above raw materials into a vessel, stir at high speed for 10 minutes for them to blend fully and disperse uniformly, and the final product will be obtained after milling in a sand mill to make the fineness less than 15 micron.

Example 12

Preparation of the Alcohol-Soluble Resin of the Present Invention

Weigh the raw materials according to the following content ratio:

Constituent A:

| | |
|---|---|
| vinyl acetate | 40 kg |
| methyl acrylate | 4 kg, |

With 10 kg of isopropyl alcohol as diluent;

Constituent B:

| | |
|---|---|
| vinyl acetate | 40 kg |
| hydroxypropyl acrylate | 2 kg |
| methyl acrylate | 4 kg |
| methacrylic acid | 5 kg |
| glycidyl methacrylate | 5 kg |
| azodiisobutyronitrile | 0.6 kg |

Constituent C:

0.2 kg of azodiisobutyronitrile dissolved in 5 kg of solvent of ethyl acetate;

With 20 kg of ethyl acetate and 65 kg of industrial alcohol as diluent, and prepared according to the same method as that of Example 1, 200.8 kg of resin with 50% of solid content will be obtained.

Example 13

Preparation of the Alcohol-Soluble Hair Colorant of the Present Invention

Formula for producing alcohol-soluble hair colorant by use of the resin of the present invention is as follows (weight ratio):

| | |
|---|---|
| resin solution prepared in Example 12 (50% of solid content) | 40 kg |
| dye | 10 kg |
| distilled water | 15 kg |
| absolute alcohol | 15 kg |
| flavor | 0.05 kg |

Process for producing the alcohol-soluble hair colorant by use of the resin of the present invention is as follows:

Put the above raw materials into a vessel, stir at high speed for 10 minutes for them to blend fully and disperse uniformly, and the final product will be obtained.

The alcohol-soluble ink prepared in Example 5 is tested according to the ink standard of QB/T2024-94, and the result is shown in table 1.

TABLE 1

The tested result of the ink of the present invention (according to ink standard of QB/T2024-94)

| | | Factual tested value | | | |
|---|---|---|---|---|---|
| Tested item | Standard value | Resin ink of Example 1 | Resin ink of Example 2 | Resin ink of Example 3 | Method for test |
| Fineness μm | ≦25 | 15 | 15 | 15 | GB/T 13217.3 |
| Viscosity S | 25~70 | 30 | 33 | 37 | GB/T 13217.4 |
| Initial dryness mm | 20~50 | 40 | 32 | 33 | GB/T 13217.5 |
| Adhesive strength % | ≧85 | 90 | 94 | 95 | GB/T 13217.7 |
| Amount of residual solvent mg/m$^2$ | ≦30 | 12 | 15 | 17 | gas chromatography |

It can be seen in the table that the ink prepared by the resin provided in accordance with the present invention advantageously has a good adhesive strength which is much higher than 85%. It is also of low amount of residual solvent and leaves no odour. The ink prepared has been tried by many printing plants, and the results show that when printed on BOPP, PE, PA, PET films, the ink prepared by the resin of the present invention reveals excellent printing adaptability, i.e., steady printing effect in different seasons, at different temperatures and humidities, with different devices and on different printing films, and good compatibility of overprint and adhesion with the existing polyamide surface printing ink system, chlorinated polypropylene composite ink system, and polyurethane steam ink system.

In conclusion, by polymerizing the main raw material vinyl acetate together with various monomers, the present invention advantageously provides a resin of good performance and low cost. Furthermore, the range of solvent for this resin is broad, including solvents of alcohols as well as, if necessary, solvents of benzenes, esters, or ketones. Therefore, a new type of resin of good performance is provided for a variety of fine chemical products such as ink, adhesive and coatings, etc.

The invention claimed is:

1. An ink comprising:
   a pigment;
   a solvent; and
   an alcohol-soluble resin including the following raw materials:

| | |
|---|---|
| vinyl acetate | 50% to 90% by weight |
| acrylic ester and/or methacrylic ester | 4% to 35% by weight |
| reactive functional group-containing compound | 6% to 15% by weight | with an initiator of 0.1% to 1.1% by weight, wherein each of the weight percentages of the raw materials is based on the total weight of the raw materials, and polymerized in at least one of ester and alcohol solvent(s);

said reactive functional group-containing compound selected from the group consisting of acrylic acid, methacrylic acid, butane dioic acid, hydroxyethyl acrylate, hydroxypropyl acrylate, hydroxyethyl methacrylate, hydroxypropyl methacrylate, glycidyl acrylate, glycidyl methacrylate, reaction product of unsaturated acid and diepoxide, acrylamide, methacrylamide, and hydroxymethyl acrylamide; said intiator is at least one of azodiisobutyronitrile and benzoyl peroxide, wherein the alcohol-soluble resin is prepared by the following steps:

1) adding into a reactor tank constituent A comprising 40 kg of vinyl acetate, 2 kg of ethyl acrylate, 1 kg of methyl acrylate and 3 kg of methyl methacrylate, along with solvents comprising 10 kg of isopropyl alcohol and 5 kg of ethyl acetate for dilution, and heating while stirring the ingredients added into the reactor tank;

2) preparing in a dropper constituent B comprising 40 kg of vinyl acetate, 3 kg of ethyl acrylate, 1 kg of methyl acrylate, 3 kg of methyl methacrylate, 4 kg of acrylic acid, 3 kg of hydroxypropyl acrylate and 0.5 kg of azodiisobutyronitrile, after the ingredients provided in step 1) being heated up to the reflux temperature, adding the constituent B drop wise into the reactor tank over a period of 2 hours, and then allowing the reaction to proceed for 1 hour;

3) dissolving 0.2 kg of azodiisobutyronitrile in 2.5 kg of isopropyl alcohol and 2.5 kg of ethyl acetate, and adding the resulting solution drop wise into the reactor tank over a period of 0.5 hour, and then allowing the reaction to proceed for 2 hours under a constant temperature; and 4) adding 20 kg of ethyl acetate and 60 kg of industrial alcohol into the reactor tank, and then cooling down and discharging the resulting mixture in the reactor tank to obtain 200.7 kg of resin with 50% of solid content.

2. An ink comprising:

a pigment;

a solvent; and an alcohol-soluble resin including the following raw materials:

| | |
|---|---|
| vinyl acetate | 50% to 90% by weight |
| acrylic ester and/or methacrylic ester | 4% to 35% by weight |
| reactive functional group-containing compound | 6% to 15% by weight | with an initiator of 0.1% to 1.1% by weight, wherein each of the weight percentages of the raw materials is based on the total weight of the raw materials, and polymerized in at least one of ester and alcohol solvent(s);

said reactive functional group-containing compound selected from the group consisting of acrylic acid, methacrylic acid, butane dioic acid, hydroxyethyl acrylate, hydroxypropyl acrylate, hydroxyethyl methacrylate, hydroxypropyl methacrylate, glycidyl acrylate, glycidyl methacrylate, reaction product of unsaturated acid and diepoxide, acrylamide, methacrylamide, and hydroxymethyl acrylamide; said intiator is at least one of azodiisobutyronitrile and benzoyl peroxide, wherein the alcohol-soluble resin is prepared by the following steps:

1) adding constituent A into a reactor tank where constituent A includes the following:

| | |
|---|---|
| vinyl acetate | 40 kg |
| methyl acrylate | 1 kg |
| methyl methacrylate | 7 kg | with 15 kg of isopropyl alcohol as diluent;

2) preparing in a dropper constituent B which includes the following:

| | |
|---|---|
| vinyl acetate | 33 kg |
| methyl acrylate | 2 kg |
| methyl methacrylate | 8 kg |
| methacrylic acid | 3 kg |
| hydroxypropyl acrylate | 3 kg |
| glycidyl acrylate | 3 kg |
| benzoyl peroxide | 0.5 kg |

3) dissolving 0.2 kg of azodiisobutyronitrile in 2.5 kg of isopropyl alcohol and 2.5 kg of ethyl acetate; and 4) adding 20 kg of ethyl acetate and 60 kg of industrial alcohol as diluent into the reactor tank after continuously reacting for 2 hours under a constant temperature in the tank, and then cooling down and discharging the resulting mixture in the reactor tank to obtain 200.7 kg of resin with 50% of solid content.

3. An ink comprising:

a pigment;

a solvent; and an alcohol-soluble resin including the following raw materials:

| | |
|---|---|
| vinyl acetate | 50% to 90% by weight |
| acrylic ester and/or methacrylic ester | 4% to 35% by weight |
| reactive functional group-containing compound | 6% to 15% by weight | with an initiator of 0.1% to 1.1% by weight, wherein each of the weight percentages of the raw materials is based on the total weight of the raw materials, and polymerized in at least one of ester and alcohol solvent(s);

said reactive functional group-containing compound selected from the group consisting of acrylic acid, methacrylic acid, butane dioic acid, hydroxyethyl acrylate, hydroxypropyl acrylate, hydroxyethyl methacrylate, hydroxypropyl methacrylate, glycidyl acrylate, glycidyl methacrylate, reaction product of unsaturated acid and diepoxide, acrylamide, methacrylamide, and hydroxymethyl acrylamide; said intiator is at least one of azodiisobutyronitrile and benzoyl peroxide, wherein the alcohol-soluble resin is prepared by the following steps:

1) adding into a reactor tank constituent A which includes the following:

| | |
|---|---|
| vinyl acetate | 45 kg |
| methyl acrylate | 1 kg | with 15 kg of absolute alcohol as diluent;

2) preparing in a dropper constituent B which includes the following:

| | |
|---|---|
| vinyl acetate | 45 kg |
| methyl acrylate | 3 kg |
| methacrylic acid | 6 kg |
| azodiisobutyronitrile | 0.5 kg |

3) dissolving 0.2 kg of azodiisobutyronitrile in 5 kg of an ethyl acetate solvent; and 4) adding 20 kg of ethyl acetate and 60 kg of industrial alcohol as diluent into the reactor tank after continuously reacting for 2 hours under a constant temperature in the tank, and then cooling down and discharging the resulting mixture in the reactor tank to obtain 200.7 kg of resin with 50% of solid content.

* * * * *